United States Patent [19]

Repplinger et al.

[11] 4,140,770

[45] Feb. 20, 1979

[54] BENZOYLETHERS AND PROCESSES FOR THEIR PRODUCTION

[75] Inventors: Gudrun Repplinger, Königsdorf; Hans Betzing, Horrem, both of Fed. Rep. of Germany

[73] Assignee: A. Nattermann & Cie. GmbH, Nattermannallee, Fed. Rep. of Germany

[21] Appl. No.: 786,810

[22] Filed: Apr. 12, 1977

[30] Foreign Application Priority Data

Apr. 14, 1976 [DE] Fed. Rep. of Germany ....... 2616484

[51] Int. Cl.$^2$ .................. A61K 31/535; C07D 295/10
[52] U.S. Cl. .............................. 424/248.58; 544/174; 544/396; 546/184; 260/326.5 J; 424/250; 424/267; 424/274; 546/237
[58] Field of Search ............... 260/570.7, 567.6 M, 260/326.5 J, 570 R, 293.8, 268 R; 544/174, 396; 424/250, 248.58, 267, 274

[56] References Cited

U.S. PATENT DOCUMENTS

| 2,668,850 | 2/1954 | Goldberg et al. | 260/570.7 R |
| 3,312,696 | 4/1967 | Turbanti | 260/570.7 |
| 3,828,030 | 8/1974 | Kinugasa et al. | 260/570.7 R |

OTHER PUBLICATIONS

Di Paco et al., Chemical Abstracts, vol. 58, 5576–5577, (1963).

Turbanti et al., Chemical Abstracts, vol. 63, 6907, 1965.

*Primary Examiner*—Jose Tovar
*Attorney, Agent, or Firm*—Burns, Doane, Swecker & Mathis

[57] ABSTRACT

Processes for preparing benzoylethers, their acid additive salts and their quaternary ammonium salts are disclosed. These compounds have useful pharmacodynamic properties.

10 Claims, No Drawings

BENZOYLETHERS AND PROCESSES FOR THEIR PRODUCTION

SUMMARY OF THE INVENTION

In one aspect, the present invention provides benzoylethers, their acid additive salts and their quaternary ammonium salts having improved pharmacodynamic properties:

These benzoylethers have the general formula

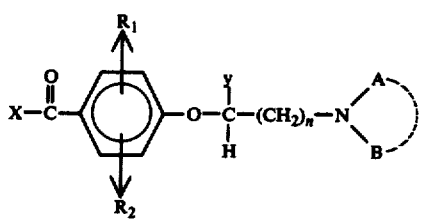

wherein X may be either

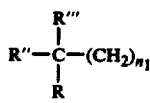

or

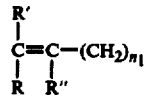

$n_1$ is an integer from 0 to 3,

R is an alkyl group having 1 to 5 carbon atoms, an aryl or aryloxy group which may be halo- or haloalkyl-substituted, a cycloalkyl or arylalkyl group, or halogen;

R' is hydrogen, a branched or straight chain alkyl group, an aryl or aryloxy group which may be halo- or haloalkyl substituted.

R" is hydrogen or an aryl group which may be halo-substituted.

R''' is hydrogen, halogen, or an alkyl group;

Y is hydrogen or an alkyl group;

A is hydrogen; a branched or straight chain alkyl group having 1 to 8 carbon atoms or an arylalkyl group wherein the alkyl group is branched or straight chain and contains 1 to 8 carbon atoms;

B is hydrogen, a branched or straight chain alkyl group having 1 to 8 carbon atoms or an arylalkyl group wherein the alkyl group is branched or straight chain and contains from 1 to 8 carbon atoms.

Furthermore the group

may be a 5 or 6 membered heterocyclic ring, which may contain an additional hetero atom such as N, O and S.

n is an integer of from 1 to 4.

$R_1$ and $R_2$ are the same group and each is a branched or straight chain alkyl group having from 1 to 4 carbon atoms.

In another aspect, the present invention provides a process for preparing these benzoylethers, their acid additive and quaternary ammonium salts by reacting an alkali metal salt of a phenol wherein the salt has the general formulae:

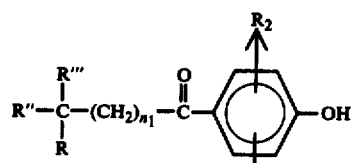

or

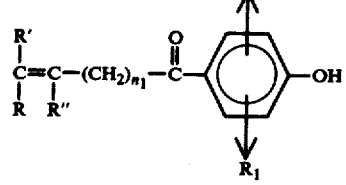

wherein M is an alkali metal atom and R, R', R", R''', $R_1$, $R_2$ and $n_1$ have the same meanings as in formula I, with a compound having the general formula

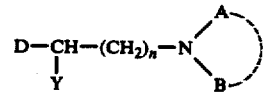

wherein Y, A, B and n have the same meanings as in formula I and D represents a halogen atom.

In another aspect, the present invention provides a process for preparing these benzoylethers, their acid additive and quaternary ammonium salts. These benzoylether may be prepared by (a) reacting phenols having the general formulae:

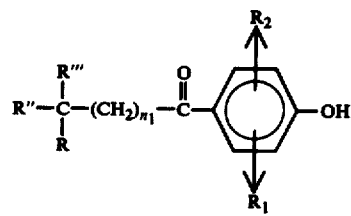

or

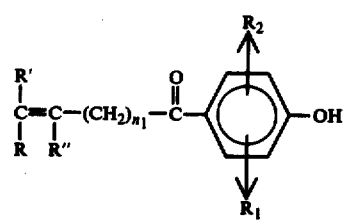

wherein R, R', R", R''', $R_1$ and $R_2$ have the same meanings as in formula I and $n_1$ represents the same number of carbon atoms as in formula I, with a chloro and bromo-substituted alkane having the general formula $$Cl-CH(Y)-(CH_2)_n-Br$$

wherein Y and n have the same meanings as in formula I, in an alkaline medium to produce bromoalkoxy-benzoyl derivatives having the general formulae:

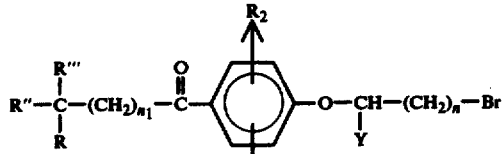

and

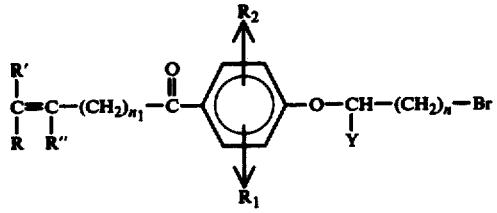

wherein R, R', R", R'", $R_1$, $R_2$, Y, n and $n_1$ have the same meanings as in formula I, (b) reacting said bromoalkoxybenzoyl derivatives with an amine having the general formula

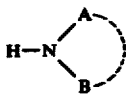

wherein A and B have the same meanings as in formula I.

DESCRIPTION OF THE PREFERRED EMBODIMENTS

The present invention provides benzoylethers and their acid additive and quaternary ammonium salts having useful pharmacodynamic properties. These benzoylethers have the general formula

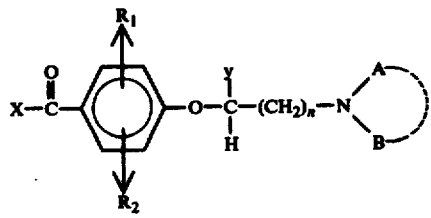   I wherein X may be either

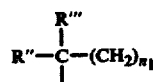

or

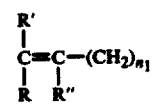

wherein $n_1$ is an integer from 0 to 3, and

R is an alkyl group having from 1 to 5 carbon atoms, an aryl or aryloxy group which may be halo- or haloalkyl-substituted, a cycloalkyl or arylalkyl group, or halogen;

R' is hydrogen, a branched or straight chain alkyl group, an aryl or aryloxy group, which may be halo- or haloalkyl substituted.

R" is hydrogen or an aryl group, the aryl group may be halo-substituted;

R'" is hydrogen, halogen, or an alkyl group;

Y is hydrogen or an alkyl group;

A is hydrogen; a branched or straight chain alkyl group having 1 to 8 carbon atoms or an arylalkyl group wherein the alkyl group is branched or straight chain and contains 1 to 8 carbon atoms;

B is hydrogen, a branched or straight chain alkyl group having 1 to 8 carbon atoms or an arylalkyl group wherein the alkyl group is branched or straight chain and contains from 1 to 8 carbon atoms.

Furthermore, the

group may also be a heterocyclic, 5- or 6-member ring, which may contain an additional hetero atom such as nitrogen, oxygen, or sulfur. Such heterocyclic groups include, for example, pyrrolidine, piperidine, piperazine, morpholine, pyrazole, imidazole, and thiazole. These groups may also be substituted with an alkyl, aryl, and/or alkoxy group.

n is an integer of from 1 to 4.

$R_1$ and $R_2$ are the same groups and each is a branched or straight chain alkyl group having from 1 to 4 carbon atoms.

The pharmaceutically acceptable acid additive and quaternary ammonium salts of these benzoylethers may be prepared from these benzoylethers, the quaternization introducing a further substituent to the nitrogen atom of formula I. This substituent may be an alkyl group with from 1 to 6 carbon atoms or an arylalkyl group optionally substituted by halogen, $NO_2$, alkoxy or alkyl. Acid additive salts include, for example, oxalates, fumarates, dichloroacetates, chlorides. Quaternary ammonium salts of these compounds include, for example, halides such as iodides, bromides, chlorides, tosylates and alkylsulfates such as methosulfates.

The compounds of formula I may be prepared by first acylating dialkylphenols with the respective acid chlorides having the general formulae:

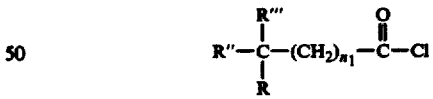

or

In these formulae R, R', R", and R'" have the same meanings as in formula I and $n_1$ represents the same number of carbon atoms as in formula I. Suitable acid chlorides include, for example, 3,3-diphenylpropionic acid chloride, p-chlorophenoxyisobutyric acid chloride, 3,3-bis(p-chlorophenyl)-propionic acid chloride, 2-phenylcinnamic acid chloride, phenylcyclohexylacetic acid chloride, cinammic acid chloride, 2-phenylbutyric acid chloride.

The dialkylphenols are acylated in the 4-position to produce new compounds having the formulae:

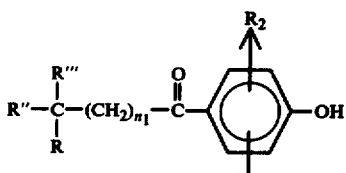

or

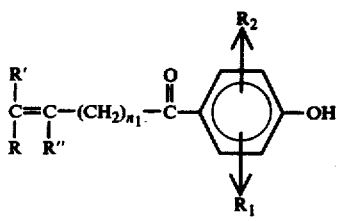

The acylation takes place in a suitable solvent such as chlorobenzene, nitrobenzene or dichloroethane and in the presence of a Lewis acid, preferably AlCl₃, by means of the "FRIEDELCRAFTS" reaction as disclosed by P. H. Gore in *Chem. Reviews* 55, (1955) and E. Berliner in *Org. Reactions* 5, 229–89 (1949).

Alternatively, the dialkylphenols may be reacted with the respective acid chlorides in a solvent such as chloroform or tetrahydrofuran in the presence of a base such as a tertiary amine, preferably triethylamine, to form an ester having the general formula:

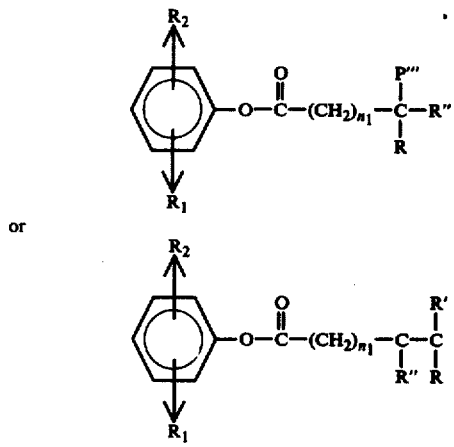

wherein R, R', R", R''' and R₁ and R₂ have the same meanings as in formula I and n₁ represents the same number of carbon atoms as in formula I.

These esters may subsequently be rearranged according to "FRIES" as disclosed by A. H. Blatt in *Org. Reactions I*, 342 (1942), in a suitable solvent, preferably chloroform, in the presence of aluminum chloride, to form the acylated phenols of formulae II and III.

The benzoylethers of the present invention may then be prepared by (a) reacting the acylated dialkylphenols of formula II or III with a chloro- and bromo-substituted alkane having the general formula

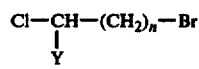

wherein Y and n have the same meanings as in formula I, in an alkaline medium to produce bromoalkoxy-benzoyl derivatives having the general formulae:

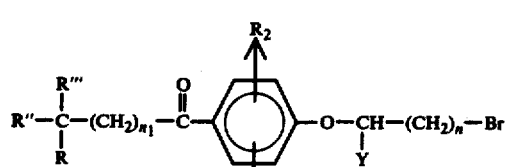

and

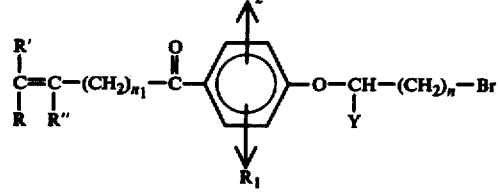

wherein R, R', R", R''', R₁, R₂, Y, n and n₁ have the same meanings as in formula I, and (b) reacting the bromoalkoxybenzoyl derivatives with an amine having the general formula

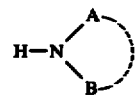

wherein A and B have the same meanings as in formula I to produce the benzoylethers of formula I.

The first step of this process may be conducted in a solvent, preferably acetone, and in the presence of a base such as potassium carbonate. The second step is carried out in a suitable solvent such as dioxane, acetone, or methyl ethyl ketone, and preferably in the presence of a base such as potassium carbonate. The benzoylethers prepared by this process may be reacted with a suitable acid to form pharmaceutically acceptable acid additive salts, e.g. with oxalic, fumaric, dichloroacetic or hydrochloric acid.

The benzoylethers prepared by this process may be further converted into the quaternary ammonium salts by reaction with (a) alkylhalides such as ethylchloride, ethylbromide, or methyliodide, (b) dialkylsulfates such as dimethylsulfate or diethylsulfate, (c) alkyl or arylalkyl tosylates or (d) arylalkylhalides such as benzyl chloride or dichlorobenzyl chloride. This reaction may be carried out in a suitable solvent, such as methanol, ethanol, or acetone.

The benzoylethers may also be prepared by reacting an alkali metal salt of a phenol wherein the salt has the general formula

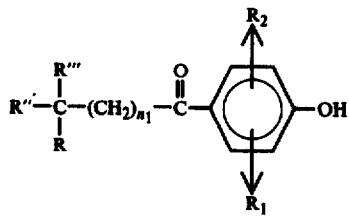

or

-continued

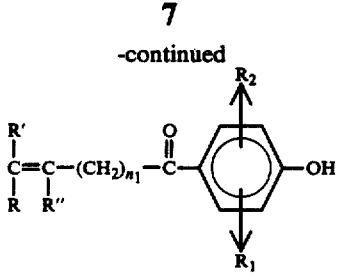

wherein M is an alkali metal atom such as sodium or potassium, R, R', R", R''', R$_1$, R$_2$ and n$_1$ have the same meanings as in formula I, with an amino alkylhalide having the general formula

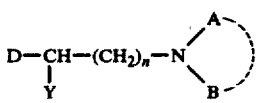

wherein Y, A, B and n have the same meanings as in formula I and D represents a halogen atom. In a preferred embodiment of the present invention, D is chlorine.

The alkali metal salt of the phenol is prepared by reacting in the presence of a solvent such as acetone, methyl ethyl ketone, toluene, or benzene, the phenols of formulae II or III with an alkali metal basic compound such as sodium amide, sodium hydride or sodium carbonate and the respective potassium compounds.

The alkali metal salt of the phenol is then condensed with the amino alkylhalides of formula IV to form the benzoylethers.

The amino alkylhalides of formula IV are preferably prepared by condensing a hydroxyalkyl halide having the general formula

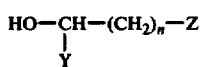

wherein Y and n have the same meanings as in formula I and Z represents a halogen, with an amine having the general formula

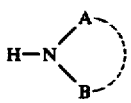

wherein A and B have the same meanings as in formula I, in a suitable solvent, preferably dioxane, to form a compound having the general formula

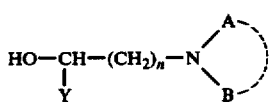

The compound of formula V is then halogenated with inorganic acid halides, such as thionyl chloride, boron trifluoride, phosphorus oxychloride or phosphorus pentachloride, in a suitable solvent, such as chloroform, ether, toluene or benzene, and thus is transformed into the amino alkylhalide of formula IV.

The following compounds may be prepared by means of these processes:

4-[2-(N,N-diethylamino)-ethoxy]-3,5-dimethyl-$\beta$-phenylpropiophenone
4-[2-(N,N-diethylamino)-ethoxy]-3,5-dimethyl-$\beta$,$\beta$-diphenylpropiophenone (hydrochloride: hereinafter "BC 58")
4-[2-piperidino-ethoxy]-3,5-dimethyl-$\beta$,$\beta$-diphenylpropiophenone
4-[2-(N,N-diisopropylamino)-ethoxy]-3,5-dimethyl-$\beta$,$\beta$-diphenylpropiophenone (hydrochloride: hereinafter "BC 79") 4-[2-morpholino-ethoxy]-3,5-dimethyl-$\beta$,$\beta$-diphenylpropiophenone
4-[2-(N,N-dimethylamino)-ethoxy]-3,5-dimethyl-$\beta$,$\beta$-diphenylpropiophenone (hydrochloride: hereinafter "BC 77")
4-[2-(N,N-diisopropylamino)-ethoxy]-3,5-dimethyl-$\alpha$-ethyl-$\alpha$-phenylacetophenone
4-[2-(N,N-diethylamino)-ethoxy]-3,5-diisopropyl-$\beta$,$\beta$-diphenylpropiophenone
4-[2-(N,N-diethylamino)-ethoxy]-3,6-dimethyl-$\beta$,$\beta$-diphenylpropiophenone
4-[2-(N,N-diethylamino)-ethoxy]-3,5-dimethyl-$\alpha$,$\alpha$-diphenylacetophenone
4-[2-morpholino-ethoxy]-3,5-dimethyl-$\alpha$-phenyl-$\alpha$-cyclohexyl-acetophenone
4-[2-(N,N-diethylamino)-ethoxy]-3,5-dimethyl-$\alpha$-ethyl-$\alpha$-phenylacetophenone
4-[2-(N,N-diethylamino)-ethoxy]-3,5-dimethyl-$\alpha$-methyl-$\alpha$-p-chlorophenoxypropiophenone
4-[2-morpholino-ethoxy]-3,5-dimethyl-$\beta$-phenylpropiophenone
4-[2-(N,N-diethylamino)-ethoxy]-3,5-dimethyl-$\alpha$-phenyl-$\alpha$-cyclohexylacetophenone
4-[2-(N,N-dibenzylamino)-ethoxy]-3,5-dimethyl-$\beta$,$\beta$-diphenylpropiophenone 4-[2-(N,N-diethylamino)-ethoxy]-3,5-dimethyl-$\beta$,$\beta$-bis-(p-chlorophenyl)-propiophenone
4-[2-pyrrolidino-ethoxy]-3,5-dimethyl-$\beta$,$\beta$-diphenylpropiophenone
4-[2-(N,N-diethylamino)-ethoxy]-2,6-dimethyl-$\beta$,$\beta$-diphenylpropiophenone
4-[3-(N,N-dimethylamino)-propoxy]-3,5-dimethyl-$\beta$,$\beta$-diphenylpropiophenone
4-[2-(N,N-diethylamino)-ethoxy]-3,5-dimethyl-$\alpha$,$\beta$-dehydro-$\beta$-phenylpropiophenone
4-[2-(N,N-diethylamino)-ethoxy]-3,5-dimethyl-$\alpha$,$\beta$-dehydro-$\alpha$,$\beta$-diphenylpropiophenone
4-[2-(N,N-dimethylamino)-1methyl-ethoxy]-3,5-dimethyl-$\beta$,$\beta$-diphenylpropiophenone
4-[2-(N,N-diethylamino)-ethoxy]-3,5-dimethyl-$\alpha$,$\beta$-diphenylpropiophenone
4-[2-(N-isopropylamino)-ethoxy]-3,5-dimethyl-$\beta$,$\beta$-diphenylpropiophenone
4-[2-(N,N-dibutylamino)-ethoxy]-3,5-dimethyl-$\beta$,$\beta$-diphenylpropiophenone
4-[3-(4'-methyl-piperazino)-propoxy]-3,5-dimethyl-$\beta$,$\beta$-diphenylpropiophenone
4-[3-(N,N-diethylamino)-propoxy]-3,5-dimethyl-$\beta$,$\beta$-diphenylpropiophenone
4-[2-morpholino-ethoxy]-3,5-dimethyl-$\beta$,$\beta$-bis-(p-chlorophenyl)propiophenone
4-[2-(N-ethyl-N-butylamino)-ethoxy]-3,5-dimethyl-$\beta$,$\beta$-diphenylpropiophenone
4-[3-piperidino-propoxy]-3,5-dimethyl-$\beta$,$\beta$-diphenylpropiophenone
4-[2-(N,N-diethylamino)-ethoxy]-3,5-dimethyl-$\alpha$,$\alpha$-dichloroacetophenone 4-[2-(N,N-diethylamino)-ethoxy]-3,5-dimethyl-α-phenylbutyrophenone 4-[2-(N,N-diethylamino)-ethoxy]-3,5-dimethyl-γ-[4'-chloro-3'-methyl)-phenoxy]-butyrophenone 4-[3-(N,N-dibutylamino)-propoxy]-3,5-dimethyl-γ,γ-diphenylpropiophenone 4-[4-(N,N-diethylamino)-butoxy]-3,5-dimethyl-γ,γ-diphenylpropiophenone 4-[2-(N,N-diethyl-N-methylamino)-ethoxy]-3,5-dimethyl-diphenylpropiophenone-iodide (hereinafter BC 96 a)

4-[2-(N,N-diethyl-N-methylamino)-ethoxy]-3,5-dimethyl-diphenylpropiophenone-methosulfate (hereinafter BC 96 a)

4-[2-(N,N-diethyl-N-propylamino)-ethoxy]-3,5-dimethyl-diphenylpropiophenone-bromide.

4-[2-(N,N-diethyl-N-4'-chlorobenzylamino)-ethoxy]-3,5-dimethyl-β,β-diphenylpropiophenone-chloride.

4-[N,N-diethyl-N-benzylamino)-ethoxy]-3,5-dimethyl-β,β-diphenylpropiophenone-chloride (hereinafter BC 96 c)

The compounds of the present invention have useful pharmacodynamic properties. The main activity is a relaxing effect on the smooth muscle tissue of mammals. Accordingly, musculotropespasmolytic effects as well as vasodilatory effect in the coronary area and in the periphery area of mammals were observed. The advantages in comparison with known antispasmodic substances lie, particularly, in a longer lasting effect and in an improved pharmacodynamic activity at lower dosage levels.

The quaternary ammonium salts of the benzoylethers of the present invention are particularly characterized by the fact that they have a good effect when applied orally.

Pharmacodynamic Effect

1. Acute toxicity

|  | $LD_{50}$ mouse i.v. | (mg/kg) p.o | $LD_{50}$ rat i.v. | (mg/kg) p.o. |
|---|---|---|---|---|
| BC 58 | 60 | 1,900 | 54 |  |
| BC 96 |  | 4,316.50 |  |  |
| BC 96 a | 7.93 | 1,284.97 |  |  |
| BC 96 c | 10–12 | 2,000 approx. |  |  |
| Papaverine | 44 | 343+ | 18+ | 325+ |

2. Spasmolytic effect 2.1 MAGNUS intestine of the guinea pig (against $BaCl_2$-spasmus)

| Examples: | | |
|---|---|---|
| BC 58 | $ED_{50}$: 4.4 × $10^{-8}$ | g/ml bath |
| BC 77 | $ED_{50}$: 7.9 × $10^{-7}$ | g/ml bath |
| BC 79 | $ED_{50}$: 2.8 × $10^{-7}$ | g/ml bath |
| Papaverine | $ED_{50}$: 7.9 × $10^{-7}$ | g/ml bath |

2.2 Spasmolysis in situ of a guinea pig modified according to BROCK (against $BaCl_2$-spasmus)

| BC 58 | At 5.6 mg/kg i.v. | 55% inhibition |
|---|---|---|
|  | At 10.0 mg/kg i.v. | 67% inhibition |
|  | At 17.8 mg/kg i.v. | 88% inhibition |
| Papaverine | At 5.6 mg/kg i.v. | 5% inhibition |
|  | At 10.0 mg/kg i.v. | 8% inhibition |

-continued

|  | At 17.8 mg/kg i.v. | 57% inhibition |
|---|---|---|

+according to KOMLOS and PETOCZ, 20 Arzneimittel-Forschung 1338 (1970)

3. Increase in perfusion 3.1 LANGENDORFF heart of the guinea pig

| Examples: | |
|---|---|
| BC 58 | $ED_{50}$++: approx. 2.2 µg |
| BC 77 | $ED_{50}$: approx. 6.6 µg |
| BC 79 | $ED_{50}$: approx. 2.3 µg |
| Papaverine | $ED_{50}$: approx. 6.0 µg |

3.2 Increase in peripheral vasodilation (A.femoralis) in the case of the narcotized dog (with planimetric evaluation taking into account the duration of the effect).

| BC 58 | At 3.16 mg/kg i.v. | approx. | 400 ml × min |
|---|---|---|---|
|  | At 5.6 mg/kg i.v. | approx. | 800 ml × min |
|  | At 10.0 mg/kg i.v. | approx. | 2,200 ml × min |
| Papaverine | At 3.16 mg/kg i.v. | approx. | 100 ml × min |
|  | At 5.6 mg/kg i.v. | approx. | 250 ml × min |
|  | At 10.0 mg/kg i.v. | approx. | 180 ml × min |

The pronounced difference results, in particular from the longer duration of the effect of BC 58.

3.3. Increase in coronary vasodilation (Bretschneider catheter) in the case of a narcotized dog (with planimetric evaluation taking into account the duration of the effect).

| BC 58 | At 3.16 mg/kg i.v. | approx. | 350 ml × min |
|---|---|---|---|
|  | At 5.6 mg/kg i.v. | approx. | 680 ml × min |
| Papaverine | At 3.16 mg/kg i.v. | approx. | 50 nl × min |
|  | At 5.6 mg/kg i.v. | approx. | 75 ml × min |

4. Effect on blood pressure and heart frequency

| BC 58 | At 3.16 mg/kg i.v. | approx. | 30 mm Hg |
|---|---|---|---|
|  | At 5.6 mg/kg i.v. | approx. | 30 mm Hg |
|  | At 10.0 mg/kg i.v. | approx. | 40 mm Hg |

++a 50% increase in flow

| Papaverine | At 3.16 mg/kg i.v. | approx. | 25 mm Hg |
|---|---|---|---|
|  | At 5.6 mg/kg i.v. | approx. | 35 mm Hg |
|  | At 10.0 mg/kg i.v. | approx. | 40 mm Hg |

Change of the heart frequency

| BC 58 | At 3.16 mg/kg i.v. | approx. | – 10 pulses/min |
|---|---|---|---|
|  | At 5.6 mg/kg i.v. | approx. | – 12 pulses/min |
|  | At 10.0 mg/kg i.v. | approx. | – 24 pulses/min |
| Papaverine | At 3.16 mg/kg i.v. | approx. | + 46 pulses/min |
|  | At 5.6 mg/kg i.v. | approx. | + 49 pulses/min |
|  | At 10.0 mg/kg i.v. | approx. | + 33 pulses/min |

The administration of the compounds of the present invention is effected in the usual way, preferably orally or intravenously.

Generally, in the case of oral administration it has been found to be advantageous to administer quantities of from about 0.1 to 10 mg per kg, preferably from about 0.5 to 5 mg per kg body-weight per day of BC 58, and from 0.01 to 5 mg per kg, preferably from 0.1 to 1 mg per kg body-weight per day of the quaternary ammonium compounds, for obtaining effective results. In the case of intravenous administration the dosage of BC 58 amounts to from about 0.005 to 0.5 mg per kg, preferably from 0.02 to 0.2 mg per kg body-weight per day, and the dosage of the quaternary ammonium compounds amount to from 0.001 to 0.1 mg per kg, preferably from 0.002 to 0.02 mg per kg body-weight per day.

In spite of this it may be necessary to deviate from the amounts stated, depending on the body-weight and the condition of the subject and its individual reaction to the pharmaceutical composition as well as on the route of administration. In some cases it might suffice to use less than the above-mentioned minimum dosage level, whereas in others the upper limit stated might have to be exceeded. If greater amounts are necessary, it might be recommendable to administer several single doses e.g. 2 to 4 during the day.

For therapeutical application the compounds of the present invention can be incorporated into pharmaceutical preparations like tablets, capsules, pills, coated tablets, granules, suspensions and solutions together with inert, non-toxic pharmaceutically suitable solid or liquid carriers, or diluents. The therapeutically effective compound shall be present in a concentration of from about 1.0 to 90 percent by weight, i.e. in amounts sufficient for reaching the range of dosage stated.

The pharmaceutical preparations may be produced e.g. by blending the active components with liquid or solid carriers, or diluents, optionally with addition of emulsifying agents and/or dispersing agents. In case water is used as solvent, it may be advantageous to use an organic co-solvent.

The following carriers and adjuvants are stated by way of example: Water, non-toxic organic solvents as glycols, vegetable oils, alcohols; solid carriers as e.g. natural stone powders (e.g. kaolins, talcum), synthetic powders (e.g. silicates), sugar (e.g. lactose and dextrose); emulsifying agents, e.g. anionic and non-ionic emulsifiers (e.g. polyoxyethylene fatty acid esters, alkyl and aryl sulfonates), dispersing agents (e.g. lignin, starch, polyvinylpyrrolidone) and lubricants (e.g. magnesium stearate, stearic acid, talcum).

The present invention is further illustrated by the following examples.

EXAMPLE 1

Forty-six and thirty-seven hundredths grams (a 10% excess) of 3,3-diphenylpropionic acid chloride in 120 ml tetrahydrofuran are placed into a 500 ml round-bottom flask which is equipped with a mechanical agitator. Eighteen and three-tenths grams 2,6-dimethylphenol with 16.7 grams triethylamine in 150 ml tetrahydrofuran are added, dropwise, to this solution while stirring. The mixture is stirred for 12 hours at room temperature. The precipitated triethylamine-hydrochloride is sucked off and the tetrahydrofuran is evaporated in vacuo. The residue is taken up in ether and washed three times with water. The solvent is dried with sodium sulfate and then evaporated in vacuo. There remain 45.0 grams 3,3-diphenylpropionic acid-2,6-dimethylphenyl ester [91.2% yield]. Forty-five grams of this ester are dissolved in a 500 ml flask in 200 ml nitrobenzene. Eighteen and two-tenths grams aluminum chloride are added and the substance is stirred, excluding any humidity, with a KPG agitator. The mixture is heated to 100° C. and the components are left to react at this temperature for 1 day. The nitrobenzene is distilled off in vacuo, the residue is taken up with ether and crushed ice is added. Subsequently, the ether phase is washed well with water, dried with sodium sulfate and the ether is evaporated except for a small amount. Thirty-two grams [71.3%] 4-hydroxy-3,5-dimethyl-$\beta$,$\beta$-diphenyl-propiophenone crystallize out. Ten grams of this compound are dissolved in 80 ml dry acetone for the etherification and 25 grams water-free potash (100% excess) are added. Twelve and twenty-five hundredths grams (200% excess) diethylamine-ethylchloride, dissolved in 150 ml acetone, are added dropwise, with the exclusion of humidity, to this solution. The solution is boiled under reflux for 1 day. The potash is filtered off, the acetone evaporated in vacuo and the residue taken up in ether. The ether solution is washed in water and dried with sodium sulfate. The hydrochloride salt is precipitated with ethereal hydrochloric acid. After recrystallization from a methanol/ether solution, 9.55 grams [67.8%] 4-[2-(N,N-diethylamino)-ethoxy] -3,5-dimethyl-$\beta$,$\beta$-diphenylpropiophenone hydrochloride (Melting point of 95°–97° C.) and 4-[2-(N,N-diethylamino)-ethoxy] -3,5-dimethyl-$\beta$,$\beta$-diphenylpropiophenone fumarate (Melting point 226° C. [decomposition]), are obtained.

EXAMPLE 2

Twenty-four and four-tenths grams 2,6-dimethylphenol are dissolved in 100 ml dry tetrahydrofuran in a 300 ml Erlenmeyer flask. Twenty and two-tenths grams (28.1 ml) triethylamine are added and 34.0 grams 3-phenyl-propionic acid chloride in 120 ml dry tetrahydrofuran are added dropwise while stirring well with a magnetic agitator. The stirring is effected at room temperature until reaction is completed. Triethylaminehydrochloride is filtered off, and the solvent evaporated in vacuo. The residue is taken up with ether and washed several times with water or a sodium bicarbonate solution. After drying with sodium sulfate, 46.1 grams (89.7%) $\beta$-phenylpropionic acid-2,6-dimethylphenyl ester are obtained.

Twenty-nine and eight-tenths grams ester are dissolved in 150 ml chlorobenzene in a 250 ml flask. Fifteen and six-tenths grams aluminum chloride are added and the mixture is kept at 120° C. for one day while stirring. The chlorobenzene is distilled off in vacuo and the residue is taken up with ether. The ethereal solution is poured on ice and washed several times with water. After having concentrated the ethereal phase, a residue is obtained which is washed out with petroleum ether.

Eighteen grams (60.4%) 4-hydroxy-3,5-dimethyl-$\beta$-phenylpropiophenone are obtained.

Fifteen grams of the propiophenone derivative are dissolved in 100 ml water-free acetone. Twenty-four grams (200% excess) potash are added while stirring well. Subsequently, 24.0 grams (200% excess) diethylaminoethylchloride, dissolved in 100 ml acetone, are added dropwise. After having boiled it under reflux for 1 day, the precipitate is filtered off, the acetone evaporated and the residue taken up with dry ether. After having precipitated the hydrochloride and sucked off the residue, several recrystallizations from methanol/ether are effected. Ten grams [43.3%] 4-[2-(N,N-diethylamino)-ethoxy]-3,5-dimethyl-$\beta$-phenyl-propiophenone hydrochloride (melting point of 128° C.) are obtained.

EXAMPLE 3

Sixteen and seven-tenths grams (0.16 mol) triethylamine are added to 18.3 grams (0.15 mol) dimethylphenol, which is dissolved in 100 ml dry tetrahydrofuran, and 40.37 grams diphenylpropionic acid chloride, dissolved in 150 ml dry tetrahydrofuran, are added, dropwise, at room temperature while stirring. The components have reacted after 20 hours at room temperature.

After having sucked off the triethylaminehydrochloride, the tetrahydrofuran is evaporated in vacuo and the residue taken up with ether. The ethereal solution is washed several times with water and dried with sodium sulfate.

After evaporating the ether in vacuo, 46.9 grams [94.7%] β,β-diphenylpropionic acid-2,6-dimethylphenyl ester are obtained.

Forty-six and nine-tenths grams (0.14 mol) ester are dissolved in 200 ml chlorobenzene and, subsequently, 18.5 grams (0.139 mol) aluminum chloride are added. The mixture is stirred for 2 days at approximately 100° C. Chlorobenzene is distilled off in the vacuum, crushed ice is added to the residue and subsequently ether and then it is washed several times with water.

After drying the ether phase, the ether is evaporated in vacuo. The remaining solid product is washed several times with petroleum ether. Thirty-two and eight-tenths grams [70%] 4-hydroxy-3,5-dimethyl-β,β-diphenylpropiophenone are obtained.

Fifteen grams of the obtained phenol are mixed in 100 ml dry acetone with 14 grams of water-free potassium carbonate. While stirring well, 7.5 grams 2-chloroethyl-morpholine, dissolved in 100 ml dry acetone, are added dropwise. After boiling under reflux for 2 days, the residue is filtered off, acetone is evaporated in vacuo and the residue is taken up in ether, washed with water and dried with sodium sulfate. The free base is precipitated with ethereal hydrochloric acid as a hydrochloride. After recrystallization from hot methanol, 15 grams 4-[2-morpholino-ethoxy] -3,5-dimethyl-β,β-diphenylpropiophenone hydrochloride (Melting point of 211°-216° C.) are obtained.

EXAMPLE 4

Eleven and two-tenths grams dimethylphenol are dissolved in 100 ml tetrahydrofuran and 9.3 grams triethylamine are added. While stirring with a magnetic agitator, 21.7 grams cyclohexylphenylacetic acid chloride, dissolved in 100 ml of dry tetrahydrofuran, are added dropwise and stirring is continued for 24 hours at room temperature.

After filtering off the triethylaminehydrochloride, the tetrahydrofuran is evaporated in vacuo and the residue is taken up in ether and washed several times with water and sodium bicarbonate solution. The ethereal phase is dried with sodium sulfate and the ether is evaporated in vacuo. There remain 28 grams cyclohexyl-phenylacetic acid-2,6-dimethylphenyl ester as a solid, white substance.

These 28 grams are mixed in 150 ml chlorobenzene with an equimolar amount of aluminum chloride (11.45 grams). The mixture is stirred for 2 days at 100° C. After distilling off the chlorobenzene in vacuo, the residue is taken up in ether and ice is added. The ethereal phase is washed several times with water and dried with sodium sulfate. After evaporating the solvent, the residue is mixed with petroleum ether. The substance which crystallizes is washed several times with petroleum ether. Thirteen grams of 4-hydroxy-3,5-dimethyl-β-phenyl-β-cyclohexylacetophenone are obtained.

These 13 grams are dissolved in 100 ml dry acetone and 11.15 grams of water-free potassium carbonate are added. While stirring with the magnetic agitator, 12 grams of 2-chloroethylmorpholine are added dropwise and the solution is boiled under reflux for 10 hours.

After complete reaction, the inorganic salts are filtered off and the filtrate is evaporated to dryness. The residue is taken up in ether and washed with water. After drying with sodium sulfate, the hydrochloride is precipitated with ethereal hydrochloric acid. After recrystallization several times from acetone/ether, 6.5 grams of 4-[2-morpholino-ethoxy]-3,5-dimethyl-α-phenyl-α-cyclohexyl-acetophenone hydrochloride (Melting point range of 198°-200° C.) are obtained.

EXAMPLE 5

Fifty grams (0.41 mol) of 2,6-dimethylphenol and 40.9 grams (0.34 mol) of aluminum chloride are mixed together in 700 ml of chlorobenzene. At room temperature and while stirring with a KPG agitator, 101 grams (0.415 mol) of 3,3-diphenylpropionic acid chloride, dissolved in 300 ml chlorobenzene, are added dropwise. The reaction mixture is kept at 100° C. for 8 hours. The chlorobenzene is distilled off in vacuo, the residue is taken up in ether and ice is added. The ethereal phase is washed out with water. After drying the ethereal phase with sodium sulfate, the solvent is evaporated in vacuo. The slimy residue is mixed with petroleum ether. There remain red crystals which are recrystallized from acetone/petroleum ether or ether/petroleum ether.

Seventy-nine grams [58.5%] 4-hydroxy-3,5-dimethyl-β,β-diphenylpropiophenone (Melting point of 137° C.) are obtained.

Thirty grams of the propiophenone derivative are dissolved in 200 ml dry acetone and 75 grams water-free potash are added. While stirring with a KPG agitator, 36.75 grams diethylaminoethylchloride, dissolved in 250 ml dry acetone, are added to the solution, dropwise. After boiling under reflux for 10 hours, the phenol reacts. The solution is filtered off and the filtrate is concentrated in vacuo. The residue is taken up in ether and the solution is washed several times with water. After drying with sodium sulfate, the free base is precipitated with ethereal hydrochloric acid as the hydrochloride. After recrystallization from methanol/ether, 25.4 grams [65%] of 4-[2-N,N-diethylamino)-ethoxy]-3,5-dimethyl -β,β-diphenylpropiophenone hydrochloride (Melting point range of 95°-97° C.) are obtained. 4-[2-(N,N-diethylamino)-ethoxy]-3,5-dimethyl-β,β-diphenylpropiophenone hydrodichloroacetate (Melting point range of 88°-92° C.).

EXAMPLE 6

Sixteen and four-tenths grams of 3,5-dimethylphenol are dissolved in 100 ml chlorobenzene and 18.4 grams of aluminum chloride are added. At room temperature, 33.5 grams β-phenyl cinnamic acid chloride, dissolved in 50 ml chlorobenzene, are added dropwise and the solution is boiled at reflux for 10 days.

Chlorobenzene is distilled off in vacuo, and the residue is mixed with ice and dissolved in ether. The ethereal phase is washed with water and dried with sodium sulfate. The ether is evaporated. Thirty-nine and four-tenths grams of 4-hydroxy-3,5-dimethyl-α,β-dehydro-α,β-diphenylpropiophenone are obtained.

Nineteen and seven-tenths grams of the propiophenone derivative are mixed with 17.5 grams of water-free potash in 250 ml acetone. While stirring, 17.6 grams of diethylaminoethylchloride, which is dissolved in 100 mls of acetone, are added dropwise. The solution is boiled at reflux for 1.5 days. The precipitate is sucked off and the acetone distilled off. The residue is taken up in ether and washed with water. After drying the ethereal phase, the hydrochloride is precipitated with ethereal hydrochloric acid. The residue is sucked off and purified with acetone. Subsequently, a crystallization is effected from methanol/ether.

Nine and nine-tenths grams [35.6%] of 4-[2-(N,N-diethylamino)-ethoxy]-3,5-dimethyl-α,β-dehydro-α,β-diphenylpropiophenone hydrochloride (Melting point range of 195°–197° C.) are obtained.

EXAMPLE 7

Seventy-five and five-tenths grams of 2,6-dimethylphenol and 68 grams of aluminum chloride are mixed in 400 mls of chlorobenzene. Sixty-two and four-tenths grams of dichloroacetychloride, dissolved in 200 mls of chlorobenzene, are added, dropwise, at room temperature. The mixture is stirred with a KPG agitator and kept at 100° C. for 2 days. The chlorobenzene is distilled off and ice and ether are added to the residue. The ethereal phase is washed several times with water, dried and concentrated. The remaining substance is recrystallized from chloroform.

Sixty-two grams [55.6%] of 4-hydroxy-3,5-dimethyl-α,α-dichloroacetophenone are obtained. Twenty grams of acetophenone and 11.9 grams of potash, water-free, are mixed with 500 mls of acetone. Twenty-three and four-tenths grams of diethylaminoethylchloride in 200 mls of acetone are added dropwise. The mixture is boiled under reflux for 2 days, the precipitate is filtered off, and the solution is concentrated. It is taken up with ether, washed with water and dried with sodium sulfate. After adding ethereal hydrochloric acid, 4-[2-N,N-diethylamino)-ethoxy]-3,5-dimethyl-α,α-dichloroacetophenone hydrochloride (Melting point of 134° C.) is obtained.

EXAMPLE 8

Fourteen and nine-tenths grams of 2,6-dimethylphenol are dissolved in 300 mls of chlorobenzene and 16.2 grams of aluminum chloride are then added. While stirring, 30 grams of 4-[(4'-chloro-3'-methyl)-phenoxy]-butyric acid chloride in 200 mls of chlorobenzene are added dropwise. The reaction mixture is kept at 100° C. for 2 days. The chlorobenzene is distilled off in vacuo, crushed ice is added to the residue which is then taken up in ether. The ethereal phase is washed several times with water and the ether is evaporated in vacuo. Dark brown to beige colored crystals are crystallized from petroleum ether. After sucking off and drying, 7.8 grams 4-hydroxy-3,5-dimethyl-γ-[(4'-chloro-3'-methyl)-phenoxy] butyrophenone are obtained.

Five grams of the butyrophenone are dissolved in 100 mls of methyl ethyl ketone; 4.2 grams of water-free potash are added to this. The reaction medium is well stirred while adding dropwise 5.2 grams of diethylaminoethylchloride. This mixture is boiled under reflux for 3 days. The inorganic salts are sucked off, the methyl ethyl ketone is evaporated in vacuo, and, after taking up the residue in ether, it is washed several times with water. After drying the ethereal phase with sodium sulfate, the hydrochloride is precipitated by adding ethereal hydrochloric acid. 4-[2-N,N-diethylamino)-ethoxy]-3,5-dimethyl-γ-[4'-chloro-3'-methyl)-phenoxy]-butyrophenone hydrochloride (Melting point of 156° C.), is obtained.

EXAMPLE 9

Fifty-three grams of 4-hydroxy-3,5-dimethyl-β,β-diphenylpropiophenone (prepared as in Example 5) are dissolved in 300 mls of dry toluene. Thirty-eight and four-tenths grams (100% excess) of 1-diethylaminopropylchloride, dissolved in 100 mls of toluene, are added to this solution dropwise. At that time, 13.8 grams sodium amide, 50% in toluene suspension, are added dropwise with stirring. This mixture is boiled for two days under reflux. The precipitate is filtered and the toluene is evaporated in vacuo. The residue is taken up in ether and washed several times with water. After drying with sodium sulfate, the hydrochloride is precipitated with ethereal hydrochloric acid and it is filtered over active carbon and recrystallized from acetone/ether. 4-[3-(N,N-diethylamino)-propoxy]-3,5-dimethyl-β,β-diphenylpropiophenone hydrochloride (Melting point = 179° C.) is obtained.

EXAMPLE 10

Forty-eight and eight-tenths grams (0.2 mol) of 2-bromoethanol are dissolved in 200 mls of dioxane and 51.6 grams (0.2 mol) of dibutylamine, dissolved in 100 mls of dioxane, are added dropwise to form a discolored solution. The reaction medium is boiled under reflux for 2 days. The dioxane is distilled off in vacuo, the residue is taken up with water, a layer of ether is then added and the mixture is washed with a sodium carbonate solution. The free base (dibutylaminoethanol) will, subsequently, be in the ethereal phase. After drying with sodium sulfate, the ether is evaporated in vacuo. The free base is distilled using a high vacuum.

Fifteen and three-tenths grams of dibutylaminoethanol, together with 6.5 mls of thionylchloride, are dissolved in 200 mls of distilled chloroform for the chlorination of the amino alcohol. The mixture is boiled under reflux for three days and, subsequently, the solvent is evaporated in vacuo. The residue is washed with ether. Dibutylaminoethylchloride hydrochloride precipitates as a white substance.

Twenty-one and eight-tenths grams of 4-hydroxy-3,5-dimethyl-β,β-diphenylpropiophenone (prepared as in Example 5) are dissolved in 150 mls of water-free acetone and 18 grams of water-free potash are added. Twelve and six-tenths grams of dibutylaminoethylchloride, dissolved in 100 mls of acetone, are added dropwise. The mixture is boiled under reflux for 2 days.

After the solution has cooled, it is filtered and the filtrate is narrowed down. The residue is taken up in ether and washed with water. After drying with sodium sulfate, the hydrochloride is precipitated by adding ethereal hydrochloric acid. After recrystallization from acetone/methanol/ether, 4-[2-(N,N-dibutylamino)-ethoxy]-3,5-dimethyl-β,β-diphenylpropiophenone hydrochloride is obtained in the form of white crystals having a melting point range of 162°–164° C.

EXAMPLE 11

Fifty grams (0.15 mol) of 4-hydroxy-3,5-dimethyl-β,β-diphenylpropiophenone (prepared as in Example 5), dissolved in 200 mls of acetone, are added, with stirring, to a reaction mixture consisting of 29 grams (0.184 mol) of 1-bromo-3-chloropropane in 300 mls of acetone and 42 grams (0.304 mol) of water-free potash. The preparation is boiled under reflux for one day and the precipitate is sucked off. The acetone is evaporated, the residue taken up with ether and a little acetone and, subsequently, washed with water. The ethereal phase is dried over sodium sulfate. The solvent is evaporated in vacuo. The residue is crystallized from acetone/petroleum ether. Fifty-two and five-tenths grams [85.5%]

of 4-(3-bromopropoxy)-3,5-dimethyl-β,β-diphenyl-propiophenone are obtained.

Twenty-five grams (0.0617 mol) of the etherified propiophenone are mixed with 150 mls of dioxane and, while stirring, 5.17 grams (0.0617 mol) of N-methylpiperazine in 50 mls of dioxane are added dropwise. The solution is boiled for four days at reflux. The dioxane is evaporated in vacuo. The residue contains the hydrochloride which, for the purpose of purifying transformed into the free base by treatment with sodium carbonate in water. The base is extracted with ether and the hydrochloride is again precipitated by adding ethereal hydrochloric acid. It is recrystallized from methanol and 14.7 grams [44.2%] of 4-[3-(4'-methyl-piperazino)-propoxy]-3,5-dimethyl-β,β-diphenylpropiophenone hydrochloride, having a melting point range of 243°-248° C., are obtained.

EXAMPLE 12

Twenty-five grams of bromoethanol are dissolved in 100 mls of dioxane. Twenty and two-tenths grams of N-ethyl-butylamine are added dropwise and the mixture is boiled under reflux for 2 days. The dioxane is distilled off, and the residue is mixed with ether. A solid product forms which, for the purpose of further reaction, is transformed into the free base.

Sixteen grams of N-ethyl-butylaminoethanol are obtained. This product is dissolved in distilled chloroform and, with stirring, 14.4 grams (8.9 mls) of thionylchloride are slowly added dropwise. Then, the reaction mixture is boiled under reflux for 8 hours. The solution is evaporated to dryness and the residue is treated several times with ether and sucked off. Seventeen grams of N-ethyl-butylaminoethylchloride hydrochloride are obtained.

Twenty-eight and one-tenth grams of 4-hydroxy-3,5-dimethyl-β, β-diphenylpropiophenone (prepared as in Example 5) are dissolved with 200 mls of acetone and 13 grams of water-free potash are added. With vigorous stirring, 14 grams of ethylbutylaminoethylchloride, dissolved in 100 mls of acetone, are added dropwise. After cooling, the precipitate is sucked off and the acetone is evaporated in vacuo. The residue is taken up with ether and washed with water. After drying with sodium sulfate, ethereal hydrochloric acid is added, thus precipitating the hydrochloride. After recrystallization from methanol/ether, 4-[2-(N-ethyl-N-butylamino)-ethoxy]-3,5-dimethyl-β,β-diphenylpropiophenone hydrochloride, having a melting point range of between 164 and 166° C., is obtained.

EXAMPLE 13

Eleven and seven-tenths grams of 2,6-dimethylphenol and 12.8 grams of aluminum chloride are mixed with 300 mls of chlorobenzene. Thirty grams of 3,3-bis-(p-chlorophenyl)-propionic acid chloride, dissolved in 200 mls chlorobenzene, are added to this mixture, dropwise. The components are reacted for two days at 120° C. After complete reaction, the chlorobenzene is distilled off in vacuo, the residue is treated with ice, and ether is added. The ethereal phase is washed several times with water. The solution is dried with sodium sulfate and the ether evaporated in vacuo. The residue is crystallized with methanol/petroleum ether. Twenty-one and three-tenths grams of 4-hydroxy-3,5-dimethyl-β,β-(p-chlorophenyl)-propiophenone are obtained.

Ten grams of this propiophenone are mixed with 7 grams of water-free potassium carbonate in 200 mls of dry acetone. Four and two-tenths grams of N-(2-chloroethyl)-morpholine, dissolved in 100 mls of acetone, are added dropwise. After boiling under reflux, complete reaction is achieved. The precipitate is filtered and the acetone distilled off. The residue, after being taken up in ether, is washed with water and dried with sodium sulfate. By adding ethereal hydrochloric acid, the hydrochloride precipitates and is then recrystallized with methanol/ether.

Five and three-tenths grams [40%] of 4-[2-morpholinoethoxy]-3,5-dimethyl-β,β-bis-(p-chlorophenyl)-propiophenone hydrochloride are obtained.

EXAMPLE 14

Fifty grams (0.15 mol) of 4-hydroxy-3,5-dimethyl-β,β-propiophenone (prepared as in Example 5) are dissolved in 300 mls of acetone and added dropwise to 31.5 grams (0.184 mol) of 1-bromo-4-chlorobutane which was prepared in 200 mls of acetone with 42 grams (0.304 mol) of potassium carbonate. The reaction is completed after 3 days of reflux.

The precipitate is sucked off, the acetone drawn off and the residue taken up in ether. The precipitate is then washed with water and dried with sodium sulfate. The ether is evaporated in vacuo. Sixty-two and six-tenths grams of 4-(4-chlorobutoxy)-3,5-dimethyl-β,β-diphenylpropiophenone are obtained.

Sixty-two and six-tenths grams (0.149 mol) of phenol ether are dissolved in 300 mls of dioxane. While stirring, 10.85 grams (0.149 mol) of diethylamine, dissolved in 200 mls of dioxane, are added dropwise. The mixture is refluxed for 3 days. After the reaction, the precipitate is sucked off and the acetone evaporated in vacuo. The residue is taken up in ether and washed with water. After drying with sodium sulfate, the hydrochloride of the base is precipitated by adding ethereal hydrochloric acid. Several recrystallizations with methanol/ether are effected.

4-[4-N,N-diethylamino)-butoxy]-β,β-diphenylpropiophenone hydrochloride, having a melting point of from 168° to 169° C., is obtained.

EXAMPLE 15

Fifty grams of 2,6-diisopropylphenol and 37.4 grams of aluminum chloride are mixed in 650 mls of chlorobenzene. While stirring with a KPG agitator, 75.35 grams of 3,3-diphenylpropionic acid chloride, dissolved in 300 mls of chlorobenzene are added dropwise at room temperature. After the solution is kept for 6 hours at 100° C., the chlorobenzene is distilled off in vacuo. The residue, taken up in ether, is washed several times with water. The ethereal phase is dried with sodium sulfate and the solvent evaporated in vacuo. Seventy grams of 4-hydroxy-3,5-diisopropyl-β,β-diphenylpropionphenone are obtained.

Fifteen grams (0.0388 mol) of the propiophenone derivative are dissolved in 100 mls of dry acetone and 21.5 grams (0.1552 mol) of water-free potash are added. While stirring, 13.4 grams (0.0785 mol) of diethylaminoethylchloride, dissolved in 75 mls of acetone, are added dropwise. After stirring for 12 hours at room temperature, the mixture is filtered and the acetone evaporated in vacuo. The residue is taken up in ether, washed several times with water, and dried with sodium sulfate. Subsequently, the hydrochloride is precipitated with ethereal hydrochloric acid. The solid substance is recrystallized with methanol/ether. Thirty-five and nine tenths grams [49.5%] of 4-[(N,N-diethylamino)-ethoxy]-3,5-diisopropyl-β,β-diphenylpropiophenone hydrochloride (having a melting point range of 179° to 182° C.) are obtained.

EXAMPLE 16

Twelve grams (0.098 mol) of 3,5-dimethylphenol and 13.2 grams (0.098 mol) of aluminum chloride are mixed with 50 mls of chlorobenzene. Twenty-four and two-tenths grams (0.098 mol) of 3,3-diphenylpropionic acid chloride, dissolved in 50 mls of chlorobenzene, are added dropwise. The preparation is reacted at 100° C. After evaporation of the chlorobenzene in vacuo, the residue is taken up in ether and washed several times with water. The ethereal phase is dried with sodium sulfate and evaporated in vacuo. Fifteen and two-tenths grams [46.2%] of 4-hydroxy-2,6-dimethyl-β,β-diphenylpropiophenone are obtained.

Twenty grams (0.0605 mol) of propiophenone are dissolved in 100 mls dry acetone and 33.4 grams (0.242 mol) of potassium carbonate (water-free) are then added. While stirring, 12.9 grams (0.095 mol) of diethylaminoethylchloride, dissolved in 100 mls of acetone, are added dropwise. The reaction is effected at room temperature. The precipitate is filtered off and the acetone is evaporated in vacuo. The residue is taken up in ether and washed several times with water. After drying with sodium sulfate, the hydrochloride is precipitated with ethereal hydrochloric acid. A recrystallization is effected with methanol/ether and 4-[2-(N,N-diethylamino)-ethoxy]-2,6-dimethyl-β,β-diphenylpropiophenone hydrochloride, having a melting point range of from 135° to 137° C., is obtained.

EXAMPLE 17

Twenty-four and four-tenths grams of 3,6-dimethylphenol and 26.6 grams of aluminum chloride are dissolved in 250 mls chlorobenzene and 48.9 grams of 3,3-diphenylpropionic acid chloride, dissolved in 150 mls chlorobenzene, are added while stirring. The stirring is continued for several days at 100° C. The chlorobenzene is evaporated in vacuo, the residue is mixed with ice and ether and washed several times with water. After drying with sodium sulfate, the ether is evaporated. Fifteen and one-tenth grams of 4-hydroxy-3,6-dimethyl-β,β-diphenylpropiophenone are obtained.

Fifteen grams of propiophenone, together with 25 grams of potassium carbonate, are dissolved in 150 mls of dry acetone. While stirring, 15.6 grams of diethylaminoethylchloride in 50 mls of acetone are added dropwise. Boiling is effected under reflux, the precipitate is filtered off and the acetone is evaporated in vacuo. The residue is taken up in ether and washed several times with water. After drying with sodium sulfate, the hydrochloride is precipitated with ethereal hydrochloric acid.

After recrystallization with methanol/ether, 19.8 grams of 4-[2-(N,N-diethylamino)-ethoxy]-3,6-dimethyl-β,β-diphenylpropiophenone hydrochloride, having a melting point range of 148° to 150° C., are obtained.

EXAMPLE 18

Thirty-seven grams (0.086 mol) of 4-[2-(N,N-diethylamino)-ethoxy]-3,5-dimethyl-β,β-diphenylpropiophenone (prepared as in Example 5) are dissolved in 200 mls of absolute ethanol. While stirring, 24.4 grams of methyliodide (0.1725 mol), dissolved in 100 mls of absolute methanol, are added dropwise. The reaction is completed after 5 hours. After distilling the solvent, the residue is recrystallized with methanol/ether. Thirty grams of 4-[2-(N,N-diethyl-N-methyl)-aminoethoxy]-3,5-dimethyl-β,β-diphenylpropiophenone-iodide (having a melting point of from 209°-210° C.) are obtained.

EXAMPLE 19

Seventeen and twenty-six hundredths grams (0.0403mol) of 4-[2-(N,N-diethylamino)-ethoxy]-3,5-dimethyl-β,β-diphenylpropiophenone (prepared as in Example 5) are dissolved in 150 mls of dry acetone. Five and eight-hundredths grams (0.0403 mol) of dimethylsulfate, dissolved in 100 mls of dry acetone, are added dropwise to this solution. The reaction is completed after 4 hours. The excessive dimethylsulfate is destroyed by adding water and the sulfuric acid is neutralized with a methanolic caustic soda solution. The precipitated sodium sulfate is filtered. The filtrate is concentrated and the residue is recrystallized with acetic ester/petroleum ether.

4-[2-(N,N-diethyl-N-methyl)-aminoethoxy]-3,5-dimethyl -β,β-diphenylpropiophenone-methosulfate (having a melting point of from 118° to 121° C.) is obtained.

EXAMPLE 20

Twenty grams (0.047 mol) of 4-[2-(N,N-diethylamino)-ethoxy]-3,5-dimethyl-β,β-diphenyl-propionphenone (prepared as in Example 5) are dissolved in 150 mls of dry acetone. To this solution 11.48 grams (0.094 mol) of propylbromide, dissolved in 75 mls of dry acetone, are added dropwise. The reaction is completed after 10 hours. After distilling the solvent, the residue is recrystallized from methanol/ether. Eleven grams of 4-[2-(N,N-diethyl-N-propylamino)-ethoxy]-3,5-dimethyl-β,β-diphenylpropiophenone-bromide are obtained, having a melting point of 216° C.

EXAMPLE 21

Thirty-two and seventy-five hundredths grams (0.0763 mol) of 4-[2-(N,N-diethylamino)-ethoxy]-3,5-dimethyl-β,β-diphenylpropiophenone (prepared as in Example 5) are dissolved in 150 mls of dry acetone. While stirring thoroughly 29.8 grams (0.1526 mol) of dichlorobenzylchloride, dissolved in 100 mls of dry acetone, are added dropwise. After refluxing for 6 hours the reaction is completed.

The solvent is distilled off and the residue is recrystallized from methanol/ether. Eight grams of 4-[2-(N,N-diethyl-N-4'-chlorobenzylamino)-ethoxy]-3,5-dimethyl-β,β-diphenylpropiophenone-chloride are obtained, having a melting point of 153° C.

EXAMPLE 22

Six grams (0,014 mol) of 4-[2-(N,N-diethylamino)-ethoxy]-3,5-dimethyl-β,β-diphenylpropiophenone (prepared as in Example 5) are dissolved in 75 mls of dry acetone. While stirring 3.45 grams (0.028 mol) benzylchloride, dissolved in 75 mls of dry acetone, are added dropwise. The reaction is completed after 2 days.

The solvent is distilled off and the residue is recrystallized from methanol/ether. Five grams of 4-[N,N-diethyl-N-benzylamino)-ethoxy]-3,5-dimethyl-β,β-diphenylpropiophenone-chloride are obtained, melting at from 168° to 170° C.

The principles, preferred embodiments, and modes of operation of the present invention have been described in the foregoing specification. The invention which is intended to be protected herein, however, is not to be

We claim:
1. An antispasmodic compound of the formula:

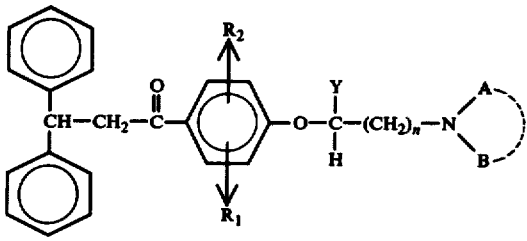

or pharmaceutically acceptable acid addition or quaternary ammonium salts thereof wherein:
Y is hydrogen or a methyl group;
n is an integer of from 1 to 4;
$R_1$ and $R_2$ are the same group and each is a branched or straight chain alkyl group having from 1 to 4 carbon atoms; and wherein

is a 5 or 6 membered heterocyclic group.

2. A benzoylether of claim 1 wherein the heterocyclic group contains a second hetero atom selected from the group consisting of nitrogen and oxygen.

3. A benzoylether of claim 1, wherein the

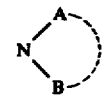

group is selected from the group consisting of a pyrrolidine, piperidine, piperazine and morpholine.

4. A benzoylether of claim 1 wherein $R_1$ and $R_2$ are methyl groups which are substituted on the benzene nucleus in the 2,6 or 3,5 or 3,6 positions.

5. A benzoylether of claim 2 wherein $R_1$ and $R_2$ are methyl groups which are substituted on the benzene nucleus in the 2,6 or 3,5 or 3,6 positions.

6. A benzoylether of claim 3 wherein $R_1$ and $R_2$ are methyl groups which are substituted on the benzene nucleus in the 2,6 or 3,5 or 3,6 positions.

7. 4-(2-pyrrolidino-ethoxy)-3,5-dimethyl-$\beta,\beta$-diphenylpropiophenone or an antispasmodic pharmaceutically acceptable salt thereof.

8. A pharmaceutical composition comprising an effective amount of a compound of claim 1 together with a carrier or adjuvant.

9. A pharmaceutical composition comprising an effective amount of a compound of claim 2 together with a carrier or adjuvant.

10. A pharmaceutical composition comprising an effective amount of a compound of claim 3 together with a carrier or adjuvant.